US011638614B2

United States Patent
Ellman et al.

(10) Patent No.: US 11,638,614 B2
(45) Date of Patent: May 2, 2023

(54) CRANIAL INSERTION PLACEMENT VERIFICATION

(71) Applicant: Mazor Robotics Ltd., Caesarea (IL)

(72) Inventors: Aviv Ellman, Kfar Sava (IL); Eli Zehavi, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 247 days.

(21) Appl. No.: 17/191,297

(22) Filed: Mar. 3, 2021

(65) Prior Publication Data

US 2021/0186626 A1    Jun. 24, 2021

Related U.S. Application Data

(62) Division of application No. 15/089,704, filed on Apr. 4, 2016, now Pat. No. 10,939,962.

(60) Provisional application No. 62/141,883, filed on Apr. 2, 2015.

(51) Int. Cl.
| | |
|---|---|
| *A61B 34/20* | (2016.01) |
| *A61B 90/00* | (2016.01) |
| *A61B 34/30* | (2016.01) |
| *A61B 17/34* | (2006.01) |
| *A61N 1/05* | (2006.01) |

(52) U.S. Cl.
CPC ............ *A61B 34/20* (2016.02); *A61B 90/361* (2016.02); *A61N 1/0534* (2013.01); *A61B 17/3403* (2013.01); *A61B 34/30* (2016.02); *A61B 2034/301* (2016.02); *A61B 2090/376* (2016.02)

(58) Field of Classification Search
CPC ....... A61B 34/20; A61B 90/361; A61B 34/30; A61B 2034/301; A61B 17/3403; A61B 2090/376; A61N 1/0534
See application file for complete search history.

(56) References Cited

U.S. PATENT DOCUMENTS

| | | | |
|---|---|---|---|
| 4,485,815 A | 12/1984 | Amplatz et al. | |
| 4,722,336 A | 2/1988 | Kim et al. | |
| 4,750,487 A | 6/1988 | Zanetti | |
| (Continued) | | | |

FOREIGN PATENT DOCUMENTS

EP    1510182    3/2005

OTHER PUBLICATIONS

Schulder, Handbook of Stereotactic and Functional Neurosurgery, 2003, pp. 360-361, Marcel Dekker Inc., USA.
(Continued)

*Primary Examiner* — Jing Rui Ou
(74) *Attorney, Agent, or Firm* — Sheridan Ross P.C.

(57) ABSTRACT

A method for verifying surgical tool placement includes attaching a guide sleeve to a surgical robot, the guide sleeve defining a guide sleeve axis; aligning the surgical robot such that the guide sleeve axis is directed at a predetermined target location; and attaching an aiming rod to the guide sleeve such that the aiming rod can rotate around the guide sleeve axis, the aiming rod having apertures along its length. The aiming rod is attached to the guide sleeve at an angle and position such that when the surgical robot is adjusted to align the guide sleeve axis with the predetermined target location, a center of each aperture of the apertures of the aiming rod and a center of the predetermined target location are collinear, independent of a rotational position of the aiming rod around the guide sleeve axis.

20 Claims, 1 Drawing Sheet

(56) References Cited

U.S. PATENT DOCUMENTS

| | | | |
|---|---|---|---|
| 4,899,756 A | 2/1990 | Sonek | |
| 5,013,317 A | 5/1991 | Cole et al. | |
| 5,016,489 A | 5/1991 | Yoda | |
| 5,078,140 A | 1/1992 | Kwoh | |
| 5,080,662 A | 1/1992 | Paul | |
| 5,143,076 A | 9/1992 | Hardy et al. | |
| 5,154,723 A * | 10/1992 | Kubota | A61B 90/11 600/102 |
| 5,257,998 A | 11/1993 | Ota et al. | |
| 5,409,497 A | 4/1995 | Siczek et al. | |
| 5,695,501 A * | 12/1997 | Carol | A61B 90/10 600/417 |
| 5,848,967 A * | 12/1998 | Cosman | G06V 30/144 600/429 |
| 5,957,933 A | 9/1999 | Yanof et al. | |
| 6,416,520 B1 | 7/2002 | Kynast et al. | |
| 7,313,430 B2 | 12/2007 | Urquhart et al. | |
| 7,803,164 B2 * | 9/2010 | Gielen | A61B 34/20 606/129 |
| 9,138,206 B2 | 9/2015 | Fischer | |
| 9,492,241 B2 | 11/2016 | Joskowicz | |
| 10,939,962 B1 | 3/2021 | Ellman et al. | |
| 2003/0167061 A1 | 9/2003 | Schlegel et al. | |
| 2004/0077939 A1 | 4/2004 | Graumann | |
| 2005/0053192 A1 | 3/2005 | Sukovic et al. | |
| 2006/0036264 A1 | 2/2006 | Selover et al. | |
| 2007/0055291 A1 | 3/2007 | Birkmeyer et al. | |
| 2009/0088634 A1 | 4/2009 | Zhao et al. | |
| 2009/0177081 A1 | 7/2009 | Ellman et al. | |

OTHER PUBLICATIONS

Official Action for U.S. Appl. No. 15/089,704, dated Mar. 8, 2018 8 pages Restriction Requirement.

Official Action for U.S. Appl. No. 15/089,704, dated Sep. 6, 2018 11 pages.

Official Action for U.S. Appl. No. 15/089,704, dated Apr. 12, 2019 13 pages.

Official Action for U.S. Appl. No. 15/089,704, dated Aug. 21, 2019 11 pages.

Official Action for U.S. Appl. No. 15/089,704, dated Apr. 13, 2020 10 pages.

Notice of Allowance for U.S. Appl. No. 15/089,704, dated Jan. 13, 2021 7 pages.

* cited by examiner

CRANIAL INSERTION PLACEMENT VERIFICATION

CROSS REFERENCE TO RELATED APPLICATIONS

This application is a divisional of U.S. patent application Ser. No. 15/089,704, filed on Apr. 4, 2016 and entitled "Cranial Insertion Placement Verification," now U.S. Pat. No. 10,939,962, issued on Mar. 9, 2021, which claims the benefit of priority of U.S. provisional application Ser. No. 62/141,883, filed Apr. 2, 2015 and entitled "Cranial Insertion Placement Verification," the entire contents of each of which are incorporated herein by reference.

FIELD

The present invention relates to the field of the insertion of surgical devices into the brain, such as electrodes for the purpose of performing Deep Brain Stimulation (DBS), and especially using imaging techniques for verifying the correct placement of the electrodes in robotically aided insertion procedures.

BACKGROUND

In order to perform DBS, a neuro-stimulator electrode is implanted in the brain, and sends out electrical impulses, typically into the subthalamic nucleus (STN) region of the brain. Other regions of the brain which may be targeted for DBS include the globus pallidus or the nucleus ventralis intermedius thalami (VIM), though the STN will be used as a typical example in this disclosure. The size of the STN is only of the order of 4 mm, such that very high placement accuracy is required, and an accuracy of 1 mm or better is desirable. There are two main methods by which placement of the DBS electrode is performed currently.

The first method is by use of a stereotactic frame using an MRI image to determine the target region into which it is desired to insert the electrode. This method is often complicated by the inability to clearly and accurately see the STN region in the MRI images.

A second method, also using a stereotactic frame, is by detection of the electrophysiological signals emitted in the STN region. The probe needle is slowly inserted into the brain along a pre-planned trajectory, and when the STN region is reached, the characteristic high-level distinctly patterned electrophysiological signal is detected. However this method too has the disadvantage that if the entry angle of the probe needle is such that the STN region is missed, it is necessary to withdraw the probe needle completely, and to retry at a different entry angle, which adds to the trauma of the procedure.

Both of the above methods require some sort of confirmation of the alignment of the stereotactic frame. One method of doing so is by use of two crosshair targets, similar to munition aiming sights, disposed on the stereotactic frame one on each side of the head. Their positions are calculated such that a straight line running between the sight centers passes through the center of the target region. Since the position of the center of the target region is known from the preoperative images, usually MRI or CT images, and since the position of the mounting of the stereotactic frame is known from these preoperative images, the position of the two crosshair targets relative to the stereotactic frame, which ensures their collinearity with the center of the target region, can be determined, and the crosshair targets mounted on the stereotactic frame accordingly. An intraoperative imaging system, such as an X-ray C-arm fluoroscope, can be maneuvered into a position such that the centers of both crosshair targets coincide in the image, which means that the intraoperative imaging system is directed along a line which also passes through the center of the target region. Therefore the probe electrode can be inserted into the cranial tissue, until its tip coincides with the center points of the overlapping images of the crosshair targets, which means that the tip is positioned at the center of the target region. The imaging procedure can be repeated in another azimuthal direction, such as approximately orthogonal to the first imaging procedure, in order to confirm that the tip of the probe electrode is also properly placed in this additional azimuthal plane orientation, and hence in all three dimensions.

Robotic implementations of cranial surgical procedures, such as those described in US published patent application No. 2009/0177081 for "Image-Guided Robotic System for Keyhole Neurosurgery", having a common inventor with the present application, have the important advantage that they obviate the need to use a stereotactic frame, and rely on the robot and its registration to preoperative images, for accurate positioning of surgical tools. Therefore, the prior art methods of using targeting sites mounted on the stereotactic frame on either side of the head, for verification of the correct cranial target location, are not relevant for use in such robotic procedures.

An additional advantage of robotic use is that when a change of target point is required, due to an intraoperative clinical decision, or due to the need to treat several target points in the same procedure, the robotic procedure makes it very easy to change target location, while it is significantly more complex to change the target location when a stereotactic frame is used, especially when also equipped with the above-mentioned aiming devices.

There therefore exists a need for a location verification system for use with such robotic surgical systems, which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems and methods for verifying the correct positioning of a robotically guided, cranially inserted surgical tool, such as an electrode probe for Deep Brain Stimulation, which has to be inserted with great accuracy into a specified region of the brain such as the STN region in the case of DBS. The system utilizes a head mounted robot used to align a guiding sleeve for the surgical probe or tool, together with a novel aiming arm, in order to perform all of the functions necessary to verify correct placement of such a probe electrode or other tool. The system can verify the position of the probe or tool, either in two dimensions, or in all three dimensions.

The system uses a novel aiming rod which incorporates two apertures through which an X-ray imaging system can view the patient's skull in the region where the surgical insertion is to be performed. Since an aiming line can be defined by the centers of two apertures, there is no need for more than two apertures on the aiming rod, though the application is intended to cover more should there be reason therefore. The aiming rod is attached at a predefined position and at a predefined angle to the robotically held surgical tool guiding sleeve, and the attachment position and angle of the aiming rod are calculated geometrically such that the line of sight through the apertures falls exactly on the targeted insertion position of the surgical tool. This targeted insertion position is defined by the robotically determined pose of the guidance sleeve, and by the depth of entry of the surgical tool or electrode probe from its externally known reference position. During the procedure of placement verification of the tip of the surgical tool or of an electrode to be implanted, the X-ray system is oriented until its line of sight passes through the center of the at least two apertures, as ascertained by confirming coincidence of the centers of the apertures in an X-ray fluoroscopic image. It is then known that the region of the brain imaged at the center of the aperture images is the insertion target position. If the tip of the surgical tool or the electrode is seen at that central position in the X-ray image, verification is thus obtained that the insertion procedure has been performed accurately, and has not been deflected from its intended path during insertion.

The above-described procedure ensures verification in one plane only. In order to verify that the position is accurate in an orthogonal, or any other angled plane, to ensure accurate placement in three dimensions, use is made of the feature that a line through the aiming rod apertures always creates a constant vector with the targeted tool tip or implant location, such that an X-ray imager centering the apertures in its image will always point at the targeted tool tip or implant location, thus enable location verification. The aiming rod can thus be rotated azimuthally around the robotic tool guiding sleeve, without changing its longitudinal position or its conical angle relative to the guiding sleeve, and one or more X-ray images obtained after rotation of the C-arm can be used to verify the position again in the new plane or planes.

There are thus advantages obtained by simple rotation of the aiming rod around the axis of the guiding sleeve, as achieved by attaching the aiming rod, via any intermediary structural elements that may be necessary, to the guide sleeve. In the detailed description section of this disclosure, that is the system configuration that is mostly described. However, it is to be understood that the system and methods can be more generally described as associating the position and orientation of the aiming rod with the activated output arm of the robot, such that the pose of the aiming rod has a known and predetermined relationship to the coordinate system of the robot, such that when the robot is adjusted so that said guide sleeve is directed at the target location, the centers of the apertures are collinear with the target location. One specific example of this configuration is by pivoting the aiming rod ultimately relative to the guide tube, such that the azimuthal angle can be readily changed, but this does not preclude the use of other support configurations for the aiming rod for single or multiple point target position verification.

Though the system has been described predominantly for use in verifying the position of an electrode probe, it is to be understood that it is also suitable for use with any similarly shaped surgical tool which has to be accurately located within the cranial volume, and in the description and associated claims, use of the term probe is intended to cover all such instruments and applications.

There is thus provided in accordance with an exemplary implementation of the devices described in this disclosure, a system for verifying the placement of a surgical tool at a preoperatively defined target location, comprising:

(i) a guide sleeve attached to the activated output element of a surgical robot, such that the axis of the guide sleeve is orientable by the robot, and (ii) an aiming rod attached to the guide sleeve, the aiming rod having apertures along its length, wherein the aiming rod is attached to the guide sleeve at an angle and position such that when the pose of the robot is adjusted such that the guide sleeve is directed at the preoperatively defined target location, the centers of the apertures and the target location are collinear.

In such a system, the collinearity of the apertures and the target location should enable an X-ray fluoroscope image taken through the apertures to verify the placement of the surgical tool at the target location. The aiming rod may be attached to the guide sleeve by means of a support arm attached to the guide sleeve at a proximal end region of the guide sleeve. In such a case, the support arm may be attached to the guide sleeve by a mounting which enables the support arm to rotate about the guide sleeve, such that the collinearity of the centers of the apertures and the target location can be verified in more than one azimuthal plane relative to the axis of the guide sleeve. In order to enable the placement of the tool to be verified, the preoperatively defined target location should be defined at a predetermined distance from a reference position on or associated with the guide sleeve.

Additionally, alternative implementations of the systems of the present disclosure may further involve a system for verifying the placement of a surgical tool at a preoperatively defined target location, comprising:

(i) a guide sleeve attached to the activated output element of a surgical robot, such that the axis of the guide sleeve is orientable by the robot, and (ii) an aiming rod attached to the activated output element of the surgical robot, the aiming rod having apertures along its length, wherein the aiming rod has a predetermined spatial and orientational relationship to the coordinate system of the robot, such that when the robot is adjusted such that the guide sleeve is directed at the preoperatively defined target location, the centers of the apertures and the target location are collinear.

Yet other exemplary implementations perform a method for verifying the placement of a surgical tool at a preoperatively defined target location, comprising:

(i) attaching a guide sleeve to the activated output element of a surgical robot, (ii) aligning the output element of the robot such that the axis of the guide sleeve is directed at the target location, and (iii) attaching an aiming rod having X-ray transparent apertures along its length to the guide sleeve, wherein the aiming rod is attached to the guide sleeve at an angle and position such that when the pose of the robot is adjusted such that the guide sleeve is directed at the preoperatively defined target location, the centers of the apertures and the target location are collinear.

Such a method may further comprise adjustment of the position of an X-ray fluoroscope imaging system such that an X-ray fluoroscope image taken through the apertures also images the target location. In such a situation, the imaging of the target location through the apertures can verify the placement of the surgical tool at the target location. In order to readily perform these methods, the aiming rod may be attached to the guide sleeve by means of a support arm attached to the guide sleeve at a proximal end region of the guide sleeve. The method may then also comprise the step of rotating the support arm about the guide sleeve, such that the imaging of the target location through the apertures can verify the placement of the surgical tool at the target location in more than one azimuthal plane relative to the axis of the guide sleeve. In all of the above-described methods, the preoperatively defined target location should be defined at a predetermined distance from a reference position on or associated with the guide sleeve.

BRIEF DESCRIPTION OF THE DRAWINGS

The present invention will be understood and appreciated more fully from the following detailed description, taken in conjunction with the drawings in which.

DETAILED DESCRIPTION

Figure 1:
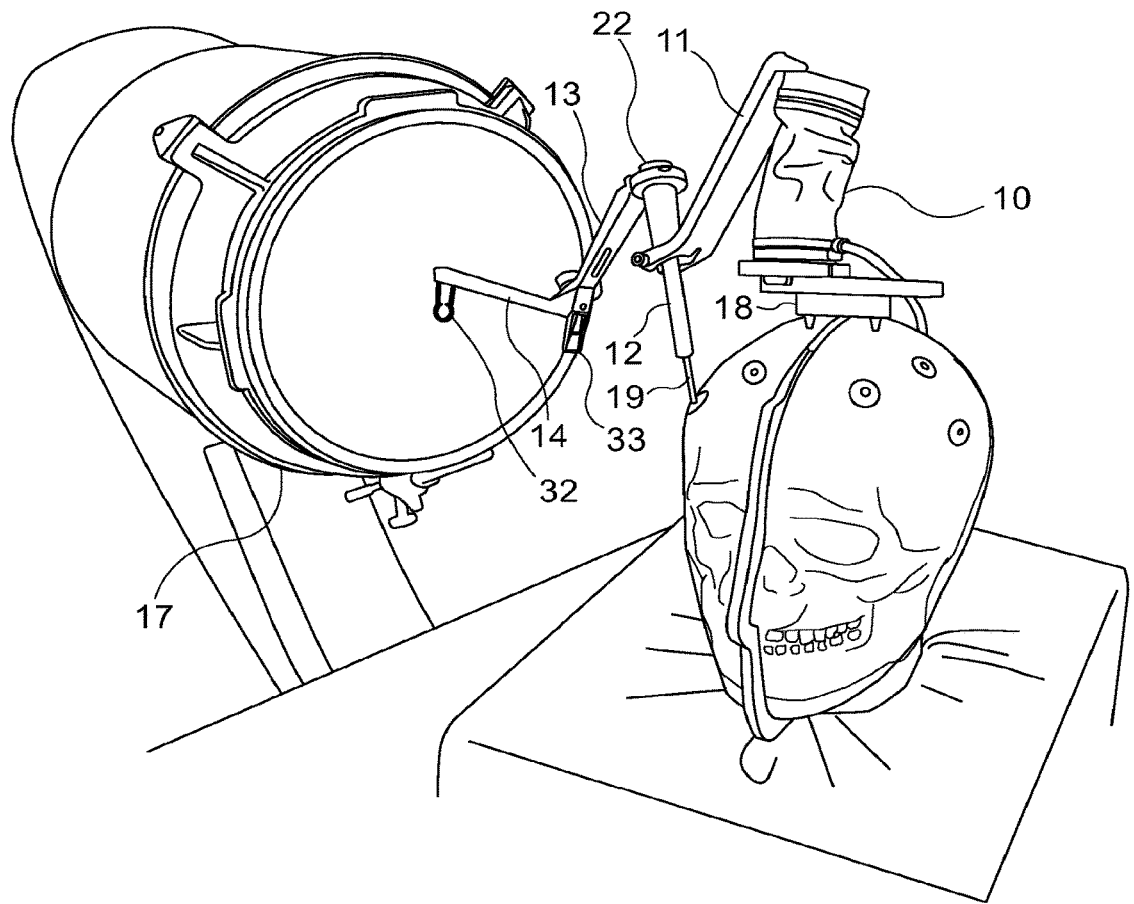
FIG. 1 illustrates schematically a model of a patient undergoing an exemplary intra-cranial insertion procedure, using robotic guidance of the surgical tool.

Reference is now made to FIG. 1, which illustrates schematically a model of a patient's skull undergoing an exemplary intra-cranial insertion procedure, using robotic guidance of the surgical tool. Although the system and method are described in terms of a DBS electrode insertion procedure, it is to be understood that the disclosure is not intended to be limited to that procedure, but can be used for any suitable cranial insertion procedure.

According to one commonly used procedure, first of all the target location for the insertion procedure is determined preoperatively by means of a series of MRI images, MRI images providing more detail than CT in such an intra-cranial, soft-tissue imaging procedure. A CT scan of the brain is then taken showing also the base 18 on which the robot 10 is to be mounted. The CT may then be merged with the MRI images, so that the preoperative plan locations performed on the MRI series is merged with the base location in the CT, so that once the robot has been mounted on that base 18, the coordinate frame of the robot can be defined in the preoperative images. The position of the targeted center of the STN region can then be converted to the robot's frame of reference, and the robot's actuating platform can be robotically oriented such that a surgical tool or probe carried by the robot can be aligned to the desired target point.

In the exemplary implementation shown in FIG. 1, insertion of the surgical tool is performed using a guide sleeve 12 attached to the robot's actuating platform by means of an attachment arm 11. The robot 10 can align the guide sleeve 12 so that it points exactly at the surgical target, which in this example, could be the center of the STN region. An electrode probe 19, or another desired tool, can now be inserted a distance predetermined from the preoperative images, such that it exactly reaches the surgical target. This predetermined distance may be conveniently measured from a reference point near the proximal end of the insertion guide sleeve 12. The terms proximal and distal are used in this disclosure with their conventional medical meanings, proximal being closest to the operator or user of the system, and furthest from the region of surgical interest in or on the patient, and distal being the region closest to the patient. Once the tool 19 has been inserted by the predetermined distance from its reference point, it is known that its distal end has reached the surgical target point.

Although the accuracy of the robotic insertion process is very high, and safeguards are used to ensure that in the event of any failure or misreading of any robotic control device, the system immediately detects such a failure, the surgeon may wish to perform an additional hands-on verification that the surgical tool, in this example case the electrode probe 19, is located in the exact planned position before finalizing its location for application of the therapeutic electrical procedure. This confirmation can be achieved by fluoroscopic X-ray viewing of the surgical site. The systems and methods of the present disclosure are able to execute this verification procedure in the following manner.

Figure 2:
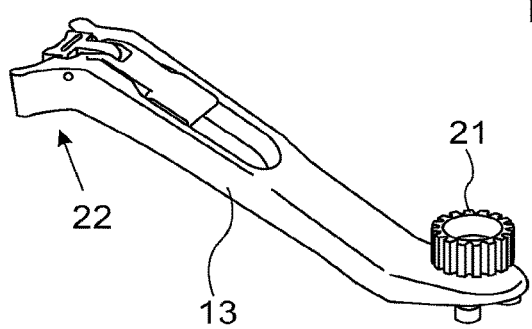
FIG. 2 shows an example of a support arm that can be used to attach an apertured aiming rod to the robot.
Figure 3:
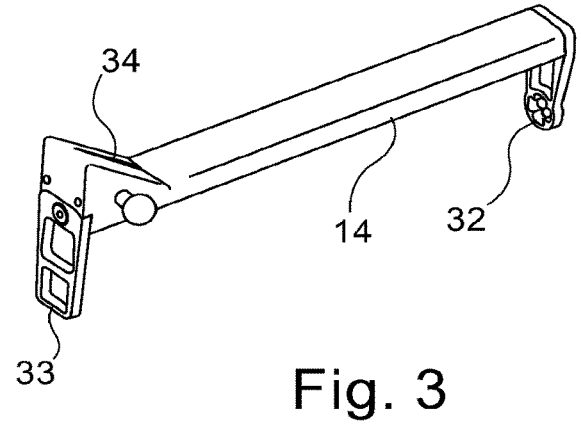
FIG. 3 illustrates schematically an apertured aiming rod used to align an X-ray imager with the surgical target point.

At the proximal end of the guide sleeve 12, a support arm 13, an example of which is shown in FIG. 2, is attached to the guide sleeve, such that it has a predetermined angle thereto. At the end of the support arm 13 opposite to that at which the support arm is attached to the guide sleeve, an aiming rod 14 is attached to the arm, such that it has a predetermined angle thereto, as shown in FIG. 3. The aiming rod 14 has aiming elements having X-ray transparent apertures 32, 33, preferably at or near its ends. The attachment of the support arm 13 may conveniently be made by means of an attachment screw 21 which mates with a threaded hole 34 at the end of the aiming rod. The angle which the aiming rod 14 makes with the support arm 13, and the length and shape of the support rod and point of attachment of the support rod 13 to the guide sleeve 12 are calculated such that geometry of the system ensures that the line running through the centers of the apertures of the aiming rod points exactly at the surgical target point, which is defined at a predetermined depth of insertion of the tool or probe down the guide sleeve. It is to be understood that the mechanical structural arrangement shown in FIG. 1 and as described in this paragraph is intended to be just one exemplary way in which to implement the fixation of the aiming rod relative to the guide sleeve of the robotic system, and that it is not meant to be a limiting arrangement. Thus, for instance, the support arm 13 could be attached to a different location on the guide sleeve 12, or even to a predetermined position on the robotic attachment arm 11, so long as its pose is defined such that the aiming rod 14 has a known spatial relationship to the robotic alignment.

In use, the physician or medical technician can now align an X-ray fluoroscope 17, usually C-arm mounted, such that the x-ray transparent centers of the aperture elements 32, 33 appear coincident in an X-ray fluoroscopic image taken along the aiming rod. Because of the above-mentioned alignment geometry of the component parts of the system, the X-ray line-of-sight running through the centers of the apertures 32, 33 of the aiming rod 14, points exactly at the surgical target point. Therefore, if the guide sleeve 12 is correctly aligned according to the preoperative surgical plan, and if the surgical tool or the electrode probe 19 has been inserted accurately down the guide sleeve by its predetermined distance, the tip of the probe or any other predefined operative point, will also be imaged on the X-ray line-of-sight at the center of the apertures. This coincidence of images of the aperture centers and the relevant tip of the probe 19 can then be used to verify that the insertion of the tool or the placement of the electrode is accurate, at least in the plane perpendicular to the line of sight of the X-ray system. If the tool or electrode is not visible, or is not central within the coincident aperture images, then the insertion is inaccurate.

According to a further implementation of the present system, in the usual situation of the support arm 13 being attached to the guide sleeve assembly 12, as shown in FIG.

1, the attachment may be made by means of a bush and sleeve joint 22, constructed such that the support arm 13 is attached at an angle relative to the guide sleeve 12, such that it can rotate azimuthally around the axis of the guide sleeve 12. If the system is now rotated around the guide sleeve 12 to another angle, even up to 90° from the initially imaged direction, and the C-arm X-ray imager is also rotated accordingly, it is possible to repeat the positioning verification procedure at the new azimuthal angle, and thus to verify the position of the electrode or tool in a plane other than that initially checked.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method for verifying surgical tool placement, comprising:
   attaching a guide sleeve to an activated output element of a surgical robot, the guide sleeve having an elongated central aperture through which a surgical tool can be extended, the elongated central aperture defining a guide sleeve axis;
   aligning the output element of the surgical robot such that the guide sleeve axis is directed at a predetermined target location; and
   attaching an aiming rod to the guide sleeve such that the aiming rod can rotate around the guide sleeve axis, the aiming rod having apertures along its length;
   wherein the aiming rod is attached to the guide sleeve at an angle and position such that when a pose of the output element is adjusted to align the guide sleeve axis with the predetermined target location, a center of each aperture of the apertures of the aiming rod and a center of the predetermined target location are collinear, independent of a rotational position of the aiming rod around the guide sleeve axis.

2. The method of claim 1, further comprising causing a position of an X-ray fluoroscope imaging system to be adjusted such that an X-ray fluoroscope image taken through the apertures of the aiming rod using the X-ray fluoroscope imaging system also images the target location.

3. The method of claim 2, further comprising verifying placement of the surgical tool at the target location based on the X-ray fluoroscope image.

4. The method of claim 3, further comprising verifying placement of the surgical tool at the target location to within an accuracy of 1 mm or less.

5. The method of claim 1, wherein attaching the aiming rod to the guide sleeve further comprises attaching a support arm to the guide sleeve at a proximal end region of the guide sleeve.

6. The method of claim 5, further comprising verifying placement of the surgical tool at the target location in more than one azimuthal plane relative to the guide sleeve axis.

7. The method of claim 1, wherein the predetermined target location is defined at a predetermined distance from a reference position on the guide sleeve.

8. The method of claim 1, further comprising inserting the surgical tool through the elongated central aperture.

9. The method of claim 8, wherein the surgical tool comprises a surgical tool tip, and the surgical tool tip comprises an electrode tip, a probe tip, or any other operative tip.

10. The method of claim 8, wherein the surgical tool comprises an electrode probe for Deep Brain Stimulation.

11. The method of claim 1, wherein the predetermined target location corresponds to a subthalamic nucleus region of a patient's brain.

12. A method of verifying surgical tool placement, comprising:
    attaching a guide sleeve to a surgical robot, the guide sleeve defining a guide sleeve axis;
    attaching an aiming rod to the guide sleeve such that the aiming rod can rotate around the guide sleeve axis, the aiming rod having apertures along its length; and
    controlling the surgical robot to position the guide sleeve such that the guide sleeve axis is directed at a predetermined target location;
    wherein the aiming rod is attached to the guide sleeve at an angle and position such that when the guide sleeve axis is directed at the predetermined target location, a center of each aiming rod aperture and a center of the predetermined target location are collinear, independent of a rotational position of the aiming rod around the guide sleeve axis.

13. The method of claim 12, further comprising extending a surgical tool through the guide sleeve and along the guide sleeve axis by a predetermined distance.

14. The method of claim 13, further comprising aligning an X-ray fluoroscope system with the center of each aiming rod aperture.

15. The method of claim 14, further comprising verifying the placement of a tip of the surgical tool at the target location using an image generated by the X-ray fluoroscope system.

16. The method of claim 15, wherein the verifying comprises verifying the placement of the tip of the surgical tool at the target location in three dimensions.

17. A surgical tool placement verification method comprising:
    manipulating a guide sleeve using a robotic arm to align an axis of the guide sleeve with a predetermined target location within a patient anatomy, the guide sleeve having an aiming rod rotatably attached thereto and the aiming rod comprising at least two apertures along its length, wherein the aiming rod is attached to the guide sleeve at an angle and position such that when the axis is directed at the predetermined target location, a center of the at least two apertures and a center of the predetermined target location are collinear, independent of a rotational position of the aiming rod around the guide sleeve axis;
    aligning an X-ray fluoroscopy system with the at least two apertures and the predetermined target location;
    obtaining an X-ray image of the predetermined target location with the X-ray fluoroscopy system; and
    verifying, using the X-ray image, a placement of a tip of a surgical tool at the predetermined target location, the surgical tool extending through the guide sleeve and along the guide sleeve axis.

18. The method of claim 17, wherein the verifying comprises verifying the placement of the tip of the surgical tool in at least two dimensions.

19. The method of claim 17, wherein the obtaining comprises obtaining a first X-ray image of the predetermined target location with the aiming rod in a first rotational position relative to the guide sleeve, and a second X-ray image of the predetermined target location with the aiming rod in a second rotational position relative to the guide sleeve.

20. The method of claim 17, wherein the predetermined target location is identified in at least one of an MRI image or a CT image.

* * * * *